US006252053B1

(12) United States Patent
Ohbayashi et al.

(10) Patent No.: US 6,252,053 B1
(45) Date of Patent: Jun. 26, 2001

(54) ENZYME-ANTIBODY COMPLEX AND A METHOD FOR MANUFACTURING THE SAME

(75) Inventors: Hirokazu Ohbayashi; Yuriko Kitano, both of Tokyo; Takashi Kitoh, Saitama-ken, all of (JP)

(73) Assignee: Nichirei Corporation (JP)

( * ) Notice: Subject to any disclaimer, the term of this patent is extended or adjusted under 35 U.S.C. 154(b) by 0 days.

(21) Appl. No.: 09/268,748

(22) Filed: Mar. 17, 1999

(30) Foreign Application Priority Data

Sep. 16, 1998 (JP) .................................................. 10-279319

(51) Int. Cl.[7] ........................... C12N 11/06; C07K 17/06; G01N 33/535
(52) U.S. Cl. ....................... 530/391.3; 435/794; 435/188; 435/960; 530/391.5
(58) Field of Search .................................... 435/188, 7.94, 435/960; 530/391.3, 391.5

(56) References Cited

U.S. PATENT DOCUMENTS

| 5,053,520 | * | 10/1991 | Bieniarz et al. | ..................... 548/520 |
| 5,057,313 | | 10/1991 | Shih et al. . | |
| 5,084,560 | * | 1/1992 | Hellstrom et al. | ................. 424/85.91 |
| 5,658,741 | | 8/1997 | Bolton et al. | .......................... 435/7.2 |

OTHER PUBLICATIONS

Pierce Catalog 1994–1995, a Perstorp Biotec Company, pp. T–155,T–157, T–163–T–165, T–169, T–170, T–188–T–191, T–214 and T–215.*
A. Blair et al, J. Immunolog. Methods, 59 (1983), 129–143.*
R. Haugland, Methods in Molecular Biology, vol. 45, 235–243: Monoclonal Antibody Protocols, Ed. W. Davis, Humana Press Inc. Totowa, NJ, 1995.*
N. Shimizu, JPAB JP10084959A, Apr. 1998.*
N. Shimizu, JPAB JP407216000A, Aug. 1995.*
O. Siiman, EPAB WO009524631A1, 1994.*
Database WPI, Week 199038, Derwent Publications Ltd., London, GB, AN 1990–286254; & JP 02 201162 A (Teijin Ltd).
Database WPI, Week 199127, Derwent Publications Ltd., London, GB, AN 1991–196013; & JP 03 089165 A (Meidensha Corp).
Database WPI, Week 199121, Derwent Publications Ltd., London, GB, AN 1991–153208; & JP 03 089164 A (Meidensha Corp).
Database WPI, Week 199015, Derwent Publications Ltd., London, GB, AN 1990–113509; & JP 02 066459 A (Sekisui Chem Ind Co Ltd).
Database WPI, Week 198643, Derwent Publications Ltd., London, GB, AN 1986–281802; & JP 61 205863 (Meidensha Elec MFG).
Database WPI, Week 198406, Derwent Publications Ltd., London, GB, AN 1984–034233; & JP 58 225028 A (Otsuka Pharm Co Ltd).

* cited by examiner

*Primary Examiner*—Mary E. Ceperley
(74) *Attorney, Agent, or Firm*—Burns, Doane, Swecker, & Mathis, L.L.P.

(57) ABSTRACT

The present invention relates to an enzyme-antibody complex where one or more molecule(s) of enzyme into which a maleimide group or a thiol group is introduced is/are covalently conjugated to a carrier (polylysine, aminodextyan and so forth) in which a thiol group when a maleimide group is introduced into the enzyme or to a maleimide group when a thiol group is introduced into the enzyme via them, and a maleimide group is introduced into at least one amino group remaining in the above complex and is covalently conjugated to a maleimide group of the above complex via a thiol group obtained by reduction of antibody fragment or antibody. The resulting complex is useful as an enzyme-labeled antibody particularly in immunohistochemistry and in enzyme immunoassay and makes an immunoassay with high sensitivity possible.

11 Claims, 1 Drawing Sheet

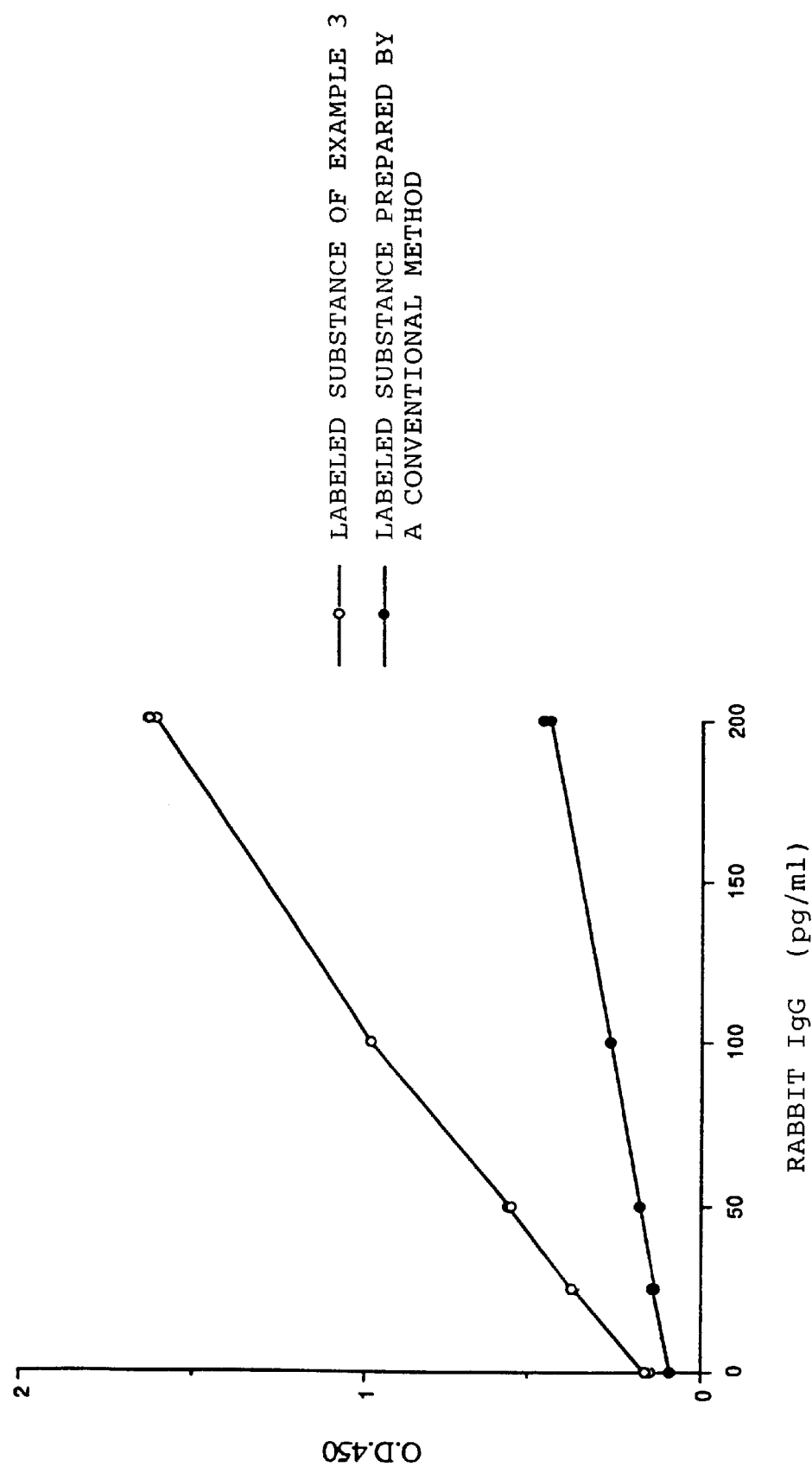

ENZYME-ANTIBODY COMPLEX AND A METHOD FOR MANUFACTURING THE SAME

DETAILED DESCRIPTION OF THE INVENTION

1. Technical Field of the Invention

The present invention relates to an enzyme-antibody complex which is covalently conjugated via a carrier and said complex is utilized in immunohistochemistry and in immunoassay such as an enzyme immunoassay.

2. Prior Art

As a result of a recent progress in immunochemistry, an immunoassay where substances in small amounts are detected with a high sensitivity using an antigen-antibody reaction have been widely used. In the field of immunohistochemistry for example, a specific substance on a tissue section can be detected using an antibody which recognizes said substance. The means therefor is that, at first, an antibody (the primary antibody) which specifically recognizes the specific substance to be detected is made to react on the tissue section. When enzyme is conjugated to the primary antibody at that time, a chromogenic substrate is colored due to its enzymatic activity whereby detection of the specific substance is possible. Practically however, in this system, the sensitivity is low and, in addition, labeling of the enzyme to various primary antibodies actually requires a lot of labor and is difficult whereby that is not a common method.

Therefore, usually, after the reaction with the primary antibody, a reaction with the secondary antibody which specifically binds to the antibody is conducted. As a result thereof, several kinds of the secondary antibody may be prepared corresponding to the animal species of the primary antibody. In that case, when a sample whereby an enzyme can be directly bound to the secondary antibody is used, the substrate is colored by the enzymatic activity whereby the detection can be conducted. However, even in such a system, sensitivity is still low and, therefore, attempts have been made.

Usually, the secondary antibody where a plurality of biotins are conjugated is used and is further made to react with a substance (an enzyme reagent) prepared by conjugating an enzyme with streptavidin which specifically binds to biotin whereupon numbers of the enzyme binding per molecule of the secondary antibody are amplified to detect the specific substance in good sensitivity. Another amplifying method which is used is that where a complex in which streptavidin is conjugated with much enzyme is previously produced and then made to react with the secondary antibody to which biotin is conjugated. As such, it is possible to detect a specific substance on a tissue section using an antibody. In that operation, the processes of 1) reaction with the primary antibody, 2) reaction with the secondary antibody, 3) reaction with an enzyme reagent and 4) coloration are necessary. If an enzyme-labeled secondary antibody of a high quality is available in that case, staining can be conducted by an operation consisting of 1) reaction with the primary antibody, 2) reaction with an enzyme-labeled secondary antibody and 3) coloration where one step is eliminated as compared with the conventional methods.

In addition, an enzyme immunoassay using two kinds of antibody makes the detection of a specific substance (analyte) with a good sensitivity possible. In detecting the specific substance by an enzyme immunoassay, the following operations are necessary. Thus, 1) antibody (the primary antibody) binding to a specific substance (analyte) is immobilized on a microtiter plate or on polystyrene beads, 2) then the plate or the beads is/are blocked by protein such as albumin, 3) a solution containing the specific substance (analyte) is added and made to react for a predetermined period, 4) enzyme-labeled antibody (the secondary antibody) specifically binding to a specific substance (analyte) is added and made to react for a predetermined period, and 5) a chromogenic substrate for the enzyme is added and the resulting degree of coloration is measured by a spectrophotometer. Incidentally, a washing operation is included between the respective steps.

Amount of the specific substance (analyte) is correlated with the enzymatic activity of the labeled enzyme of the secondary antibody bound to said substance and, therefore, it is possible to determine the amount of the specific substance (analyte) by means of the degree of coloration. The antibody used here may be any of monoclonal antibody and polyclonal antibody. In the case of monoclonal antibody however, it is necessary that the antibody used for immobilization and the antibody which is to be labeled bind to different sites of said specific substance (analyte). Unlike in the case of immunohistochemistry, it is common in an enzyme immunoassay that enzyme is directly labeled to the secondary antibody and no amplifying operation is conducted. Accordingly, sensitivity of that measuring system is greatly dependent upon the quality of the enzyme-labeled secondary antibody.

When an enzyme-labeled antibody of a high quality is obtained as such, it is now possible to stain in less steps in the field of immunohistochemistry and also to conduct a measurement with higher sensitivity in an enzyme immunoassay.

3. Problems to be Solved by the Invention

Accordingly, an object of the present invention is to newly offer an enzyme-labeled antibody of a high quality.

BRIEF EXPLANATION OF THE DRAWINGS

The attached drawing shows the result of Example 5 of the present invention.

1. Means to Solve the Problems

The present inventors have conducted an investigation on a method for the manufacture of an enzyme-antibody complex for obtaining an enzyme-labeled antibody of a high quality and have found that such an object can be achieved by conjugating the enzyme to the antibody via a carrier. As a result of further study, they have accomplished the present invention.

Thus, the present invention relates to an enzyme-antibody complex where one or more molecule(s) of enzyme into which a maleimide group or a thiol group is introduced is/are covalently conjugated to a carrier in which a thiol group when a maleimide group is introduced into the enzyme or a maleimide group when a thiol group is introduced into the enzyme via them, and a maleimide group is introduced into at least one amino group remaining in the above complex and is covalently conjugated to antibody or antibody fragment via thiol group obtained by reduction of them. The present invention also relates to a method for the manufacture of an enzyme-antibody complex comprising a step where enzyme into which a maleimide group or a thiol group is introduced is covalently conjugated to a carrier in which a thiol group when a maleimide group is introduced into the enzyme or a maleimide group when a thiol group is introduced into the enzyme via them, and a step where a maleimide group is introduced into at least one amino group remaining in the above complex and the reduced antibody or antibody fragment is covalently conjugated thereto via a thiol group. The present invention will be further illustrated as hereunder.

Although the present invention has been at first conducted during the course of investigating the enzyme-antibody complex which can be used in the field of immunohistochemistry and enzyme immunoassay, there is no restriction for applying it to other fields.

There is no particular limitation for the carrier of the present invention so far as it is a substance having at least two amino groups. However, in order to enhance the sensitivity of the immunoassay, it is recommended that many enzymes and antibodies are conjugated to a carrier. Accordingly, it is necessary that the carrier has a molecular weight to a satisfactory extent and has many amino groups. Examples of the preferred carrier achieving such an object are peptide polymer and/or polysaccharide having many amino groups preferably having a molecular weight of 5,000–500,000 or, more preferably, 10,000–300,000. However, the above-mentioned range of the molecular weight is just a rough yardstick. Therefore, substances having more molecular weight than the above range may be used so far as neither precipitation nor sedimentation is resulted in a solution and, if an object of the present invention can be achieved, substances having less molecular weight than the above range may be used as well.

In the present invention, a peptide containing many amino groups having a binding ability may be appropriately used as a carrier. An example thereof is a peptide having α-amino groups, ε-amino groups and other amino groups such as lysine, arginine, ornithine, glutamine and various basic amino acids. Specific examples are polylysine which is a polymer of lysine having an ε-amino group and various peptides having other amino acids as well as many lysine molecules. Examples of the latter peptide polymer are a random copolymer of lysine with glycine, a random copolymer of lysine with serine and a random copolymer of lysine with glutamic acid which are available in market in various molecular weights.

On the other hand, a polysaccharide into which amino group is introduced may be used as a carrier in the present invention as well. Examples of the polysaccharide are dextran, agarose, dextrin, DEAE- (DEAA-, TEAE- or CM-) cellulose and soluble starch. Introduction of amino groups may be conducted by a known method whereby amino groups are introduced into a skeleton of the polysaccharide.

In the case of aminodextran for example, it may be prepared by a known method starting from dextran. An example thereof is that dextran is oxidized with sodium periodide to produce an aldehyde group, then made to react with a diamine and reduced with sodium borohydride to give a product. With regard to a molecular weight, the molecular weight of the starting dextran is suitably selected so that aminodextran of a desired molecular weight can be prepared.

With regard to the enzyme used in the present invention, any enzyme may be used so far as it has one or more amino group(s) whereby the enzymes which are commonly used in immunoassay may be appropriately used. Non-limitative examples thereof are horse radish peroxidase, alkaline phosphatase, β-galactosidase and glucose oxidase.

Then a maleimide group is introduced into such an enzyme and, for such a purpose, a compound having both a maleimide group and a succinimide ester group in a molecule is used. For example, a divalent cross-linking agent having a maleimide group at one end and an N-hydroxysuccinimide group at another end may be used and its examples are N-(6-maleimidocaproyloxy) succinimide (EMCS) and N-(4-maleimidobutyroyloxy) succinimide (GMBS). Those substances conjugate to an amino group of the enzyme to form an acid-amide bond (—NH—CO—) while a maleimide group is introduced thereinto (incidentally, this maleimide group reacts with a thiol group introduced into the carrier to form a thioether bond (—S—) as will be mentioned later).

In addition to the above-mentioned EMCS and GMBS, the following compounds may be exemplified in a non-limitative manner as the compounds having both maleimide and succinimide groups within a molecular. They are N-succinimidyl-N-maleimidoacetate, N-succinimidyl-4-(N-maleimido)butyrate, N-succimidyl-6-(maleimido)-hexanone, N-succinimidyl-4-(N-maleimidomethyl)cyclohexane-1-carboxylate, N-succinimidyl-m-(N-maleimido) benzoate, N-succinimidyl-p-(N-maleimidophenyl)-4-butyrate, N-sulfosuccinimidyl-4-(N-maleimidomethyl)cyclohexane-1-carboxylate, N-succinimidyl-m-(N-maleimido)benzoate and N-sulfosuccinimidyl-p-(N-maleimidophenyl)-4-butyrate.

Unlike in the above-mentioned case, the present invention also includes the case where a thiol group is introduced into enzyme and, in that case, a method using S-acetylmercaptosuccinic anhydride, N-succinimidyl 3-(2-pyridyldithio)propionate (SPDP), etc. has been known for introducing a thiol group into the enzyme. Those reagents react with an amino group in the enzyme and the blocked thiol group is introduced into the enzyme. After that, a treatment with hydroxylamine or with DTT is conducted when S-acetylmercaptosuccinic anhydride or SPDP is used, respectively to remove a protective group of blocked thiol group whereupon a thiol group is produced.

A method for introducing the maleimide or thiol group into a carrier is entirely same as that for introducing it into an enzyme. Reaction of maleimide group with thiol group quickly takes place whereupon they form a covalent bond. Accordingly, when an enzyme into which maleimide group is introduced is mixed with a carrier into which thiol group is introduced, they form a covalent bond. That is entirely same as in the case of an enzyme into which thiol group is introduced and a carrier into which maleimide group is introduced. When a carrier is conjugated to an enzyme, it is necessary for conjugating to the antibody later that maleimide or thiol groups are introduced in such a manner that at least one amino group is left remained in a carrier. There is no particular difficulty in setting a condition therefor and, for example, molecular numbers of reagents used for introduction of maleimide or thiol groups may be made smaller than those of the amino groups in the carrier.

The antibody used in the present invention may be any of polyclonal antibody and monoclonal antibody. With regard to a heavy chain in the antibody, each heavy chain binds with another by means of an S—S bond and such a bond is cleaved by a reducing agent to give a thiol group. Examples of the reducing agent are mercaptoethanol and mercaptoethylamine. Further, antibody gives F(ab')$_2$ as a result of digestion by pepsin and an S—S bond in said F(ab')$_2$ is cleaved by the above reducing agent to give Fab' resulting in another thiol group. Those thiol groups do not participate in an antigen-antibody binding and, in addition, they do not exist in the vicinity of the antigen-binding site. Therefore, even if conjugation to another substance via those thiol groups takes place, a binding ability to antigen is not lost. As an antigen fragment, Fab', F(abc')$_2$, Fabc', etc. may be used in addition to F(ab')$_2$.

A method for introducing a maleimide group into a carrier to which an enzyme is conjugated is as mentioned above. When an enzyme-conjugated carrier into which a maleimide group is introduced is mixed with an antibody or antibody fragment wherein a thiol group is produced by reduction, they may be easily covalently conjugated whereby an enzyme-antibody complex via a carrier is achieved.

Manufacture of an enzyme-antibody complex using poly-L-lysine as a carrier and an enzyme into which a maleimide group is introduced will be mentioned hereinafter as one of the embodiments of the present invention.

(1) Preparation of a Thiol Group-conjugated Carrier

S-Acetylmercaptoethylsuccinic anhydride is added to and made to react with a solution containing poly-L-lysine and then made to react with hydroxylamine to introduce a thiol group into a carrier (preparation of a carrier-SH). However, the carrier is not completely thiolated but some amino groups are left in a free form.

(2) Preparation of Maleimide Group-conjugated Peroxidase

Horse radish peroxidase (POD) is made to react with EMCS to prepare a peroxidase to make maleimide group-conjugated peroxidase (M-POD).

(3) Preparation of POD-poly-L-lysine Complex

A thiol group-conjugated carrier is mixed with M-POD and made to react at 4° C. for 18 hours to give a complex (carrier-SH-M-POD). As a result of this reaction, a carrier (complex) having above-mentioned SH-M-POD groups, SH groups and free amino groups into which nothing is introduced is obtained.

(4) Preparation of the Above-mentioned Complex to Which Maleimide Groups are Conjugated An EMCS solution is added to and made to react with the above-mentioned complex so that a maleimide group is introduced into a part of the free amino groups in the above complex. As a result of this reaction, a carrier (complex) having SH-M-POD groups, maleimide groups and free amino groups into which nothing is introduced is obtained.

(5) Preparation of Reduced Antibody Fragment

Goat anti-rabbit IgG is treated with pepsin to give its F(ab')$_2$ fragments and the fragments are reduced by being made to react with cysteamine to give reduced antibody fragments (SH-Fab').

(6) Preparation of an Enzyme-antibody Complex

The reduced antibody fragments and the complex prepared in (4) are mixed and made to react so that the fragments (SH-Fab') were introduced into many of the maleimide groups conjugated to the carrier to give an enzyme-antibody complex. As a result of this reaction, a carrier (enzyme-antibody complex) wherein free amino groups into which nothing is introduced remain in addition to SH-M-POD groups, M groups and S-Fab' groups introduced to a part of M are introduced is obtained.

The enzyme-antibody complex in accordance with the present invention has been firstly successful by adopting the above-mentioned structure. Thus, to begin with, numbers of the antibody (M-S-Fab') are many whereby a possibility of binding to the antigen becomes very high and, as a result, sensitivity becomes very high. In addition, numbers of the labeled enzyme (SH-M-POD) are many whereby, even if only a part of antibody binds to antigen, many labeled enzymes are conjugated thereto (in other words, there are many signals). Therefore, when it is colored, very enhanced coloration is resulted and, due to that, the sensitivity is high as well.

Consequently, in accordance with the present invention, there is a significant merit that, even in the case of a sample which is in a very small amount or in a very diluted state, a precise analysis is possible.

EXAMPLES

The present invention will now be further illustrated by way of the following examples which, however, are not intended to limit the scope of the present invention thereto.

Example 1

Manufacture of an Enzyme-carrier Complex

Maleimide group-conjugated peroxidase was prepared as follows. Thus, 5 mg of EMCS dissolved in 300 $\mu$l of DMF was added to 16 mg of horse radish peroxidase dissolved in 1.2 ml of a 0.1M sodium phosphate buffer (pH 7.5) and the mixture was made to react at room temperature for 30 minutes. After that, a gel filtration was performed using Sephadex G25 (made by Pharmacia). Then an absorbance at 403 nm was measured and the peak was collected and concentrated by means of an ultrafiltration.

Then thiol group-conjugated polylysine bonded to a thiol group was prepared as follows. Thus, 3.2 mg of S-acetylmercaptosuccinic anhydride dissolved in 20 $\mu$l of DMF was added to 4.4 mg of poly-L-lysine hydrobromide (manufactured by Sigma; molecular weight: 120,000) dissolved in 880 $\mu$l of a 0.1M phosphate buffer and the mixture was made to react at 30° C. for 20 minutes. After that, 200 $\mu$l of a 0.1M Tris buffer (pH 7) and a 1M hydroxylamine (pH 7) and 20 $\mu$l of a sodium EDTA solution (pH 7) were added thereto and the mixture was made to react at 30° C. for five minutes. Then the reaction solution was purified by a gel filtration using Sephadex G25 and the peak at an absorbance of 230 nm was collected and concentrated by means of an ultrafiltration.

Maleimide group-conjugated peroxidase and thiol group-conjugated poly-L-lysine were mixed and made to react at 4° C. for 18 hours. The reaction product was purified by a gel filtration using Ultrogel AcA44 (manufactured by Biosepra) and the absorbance at 403 nm of each fraction was measured. A complex of horse radish peroxidase with poly-L-lysine was present in a high-molecular fraction.

Example 2

Manufacture of an Enzyme-antibody Complex. 1

15 mg of EMCS dissolved in 375 $\mu$l of DMF was added to 5 mg of a complex of horse radish peroxidase with poly-L-lysine dissolved in 1.5 ml of a 0.1M sodium phosphate buffer (pH 7.5) and the mixture was made to react at room temperature for 30 minutes. The reaction product was separated by means of a gel filtration using Sephadex G25 and the peak of 403 nm was collected and concentrated by an ultrafiltration.

After that, 311 $\mu$l of a 0.1M cysteamine hydrochloride was added to 23 mg of goat anti-rabbit IgG dissolved in 2.3 ml of a 0.1M sodium phosphate buffer (pH 6) and the mixture was made to incubate at 37° C. for 1.5 hours. The reaction product was purified by a gel filtration using Sephadex G25 and the peak of 280 nm was collected and concentrated by means of an ultrafiltration. Those concentrates were mixed and made to react at 4° C. for 18 hours. The reaction product was purified by a gel filtration using Ultrogel AcA44 and the absorbances at 280 nm and 403 nm of each fraction were measured. The fractions of high molecular weight having the absorptions of both wave lengths were the enzyme-antibody complex.

Example 3

Manufacture of an Enzyme-antibody Complex. 2

15 mg of EMCS dissolved in 300 μl of DMF was added to 2 mg of a complex of horse radish peroxidase with poly-L-lysine dissolved in 1.2 ml of 0.1 M sodium phosphate buffer (pH 7.5) and the mixture was made to react at room temperature for 30 minutes. The reaction product was separated by means of a gel filtration using Sephadex G25 and the peak of 403 nm was collected and concentrated by means of an ultrafiltration.

With respect to goat anti-rabbit IgG, its $F(ab')_2$ fractions were prepared by a known method. Thus, 111 μl of a 0.1M cysteamine hydrochloride was added to 5 mg of goat anti-rabbit IgG $F(ab')_2$ dissolved in 1 ml of a sodium phosphate buffer (pH 6) and the mixture was incubated at 37° C. for 1.5 hours. The reaction product was purified by a gel filtration using Sephadex G25 and the peak of 280 nm was collected and concentrated by means of an ultrafiltration. Those concentrates were mixed and made to react at 4° C. for 18 hours. The reaction product was purified by a gel filtration using Ultrogel AcA44 and the absorbances at 280 nm and 403 nm of each fraction were measured. The fractions of high molecular weight having the absorptions of both wave lengths were the enzyme-antibody complex.

Example 4

Comparison of the Enzyme-antibody Complex Prepared in Example 3 with the Enzyme-labeled Antibody Prepared by a Conventional Method in Terms of Immunohistochemistry As the primary antibody, rabbit anti-S-100 polyclonal antibody (Nichirei) was used and staining of tissue sections of stomach was conducted. First, the tissue was sliced and adhered onto a slide glass. Then, paraffin and peroxidase were removed therefrom and, after that, a reaction with the above-mentioned primary antibody was conducted at room temperature for one hour. After well rinsing with PBS, the secondary antibody was dropped thereinto. As to the secondary antibody, that which was prepared in Example 3 was used in a concentration of 2 μg/ml. In addition, the antibody which was labeled with peroxidase by a conventional method was used in the same concentration as well. Method of labeling was conducted in accordance with that mentioned in "Enzyme Immunoassay" (third edition) published by Igaku Shoin, pages 86–92 and all of the materials and reagents used therefor were the same as those used in Example 3. Reaction with those secondary antibody was conducted at room temperature for 30 minutes.

Further, in order to compare with a streptavidin-biotin method (SAB method), a reaction with a biotin-labeled anti-rabbit polyclonal antibody (Nichirei) as the secondary antibody was conducted as well. In that case, after the reaction with the secondary antibody for ten minutes, the reaction mixture was washed and peroxidase-labeled streptavidin (Nichirei) was dropped there into followed by reacting for five minutes. After that, washing was well conducted in any of the cases, a substrate solution (diaminobenzidine and hydrogen peroxide) was dropped thereinto and made to react therewith, the mixture was well washed with pure water, sealed and observed under a microscope. The result is shown below. The enzyme-antibody complex prepared in Example 3 was far better than the directly labeled one in terms of staining strength and, in addition, better than an SAB method where an amplifying operation was conducted.

The result is shown in the following table.

| Sample | Staining Strength |
| --- | --- |
| A | ± |
| B | + + |
| C | + |

A: enzyme-labeled antibody by a conventional method
B: enzyme-antibody complex prepared in Example 3
C: streptavidin-biotin method

Example 5

Comparison in Enzyme Immunoassay Between the Enzyme-antibody Complex Prepared in Example 3 and an Enzyme-labeled Antibody Prepared by a Conventional Method To a 96-well microtiter plate was added 100 μl of goat anti-rabbit IgG of a concentration of 10 μg/ml and incubated at room temperature for two hours. After washing with a saline, 200 μl of 1% bovine serum albumin was added and incubated for two hours. Rabbit IgG of a certain concentration (0–200 pg/ml) (100 μl) was added thereto, the mixture was incubated for two hours and washed with a saline, 100 μl of the enzyme-antibody complex prepared in Example 3 or an enzyme-labeled antibody prepared by a conventional method (both in a concentration of 2 μg/ml based upon the amount of the antibody) was added and incubation was conducted for 30 hours. This was washed with a saline, 100 μl of a chromogenic substrate solution (tetramethylbenzidine and hydrogen peroxide) was added thereto and made to react therewith for 15 minutes and the reaction was stopped by adding 50 μl of 1N sulfuric acid. Degree of coloration was measured by a microplate reader. The result is as shown in FIG. 1 and the enzyme-antibody complex prepared in Example 3 was significantly better than the enzyme-labeled antibody prepared by the conventional method.

FIG. 1 shows the above result. In the drawing, an abscissa is concentration of rabbit IgG while an ordinate is absorbance at 450 nm. ○ is the enzyme-antibody complex prepared in Example 3 while ● is the enzyme-labeled antibody prepared by the conventional method.

MERIT OF THE INVENTION

The enzyme-antibody complex of the present invention is useful particularly as an enzyme-labeled antibody (not only as the primary antibody but also as the secondary antibody) in immunohistochemistry and in enzyme immunoassay and makes an immunoassay of a high sensitivity possible.

What is claimed is:

1. An enzyme-polylysine-antibody an enzyme-aminodextran-antibody complex, an enzyme-polylysine-antibody fragment complex or an enzyme-aminodextran-antibody fragment complex prepared by a method which comprises:

(1) reacting a maleimide group-introduced enzyme with a thiol group-introduced polylysine or aminodextran having molecular weight of 5,000 to 500,000 to give an enzyme-polylysine or enzyme-aminodextran; complex wherein plural molecules of the enzyme are covalently conjugated to the polylysine or aminodextran;

(2) introducing a maleimide group to at least one amino group remaining in the enzyme-polylysine or enzyme-aminodextran complex obtained in (1); and (3) reacting the maleimide group(s) of the enzyme-polylysine or enzyme-aminodextran complex prepared in (2) with a thiol group(s) generated by reducing an antibody or an antibody fragment prepared by digesting the antibody with pepsin.

2. A complex according to claim 1, wherein the enzyme is one member selected from the group consisting of horse radish peroxidase, alkaline phosphatase, β-galactosidase and glucose oxidase.

3. A complex according to claim 1, herein the antibody fragment is F(ab')$_2$.

4. A complex according to claim 2, wherein the antibody fragment is F(ab')$_2$.

5. A complex according to claim 1 in which the carrier has a molecular weight of 5,000–500,000.

6. A complex according to claim 1 in which the carrier is aminodextran.

7. A complex according to claim 6 in which the enzyme is at least one which is selected from horse radish peroxidase, alkaline phosphatase, β-galactosidase and glucose oxidase.

8. A kit for immunoassay characterized in containing the complex as recited in claim 7.

9. A kit for immunoassay characterized in containing the complex as recited in claim 1.

10. A complex according to claim 5, in which the carrier has a molecular weight of 10.000–300,000.

11. A method for manufacturing an enzyme-antibody complex, wherein said method comprises covalently conjugating an enzyme to an amine-based carrier to form an enzyme-carrier complex, wherein
  it the enzyme contains a thiol group, a maleimide group is introduced into the carrier such that the enzyme is covalently conjugated to the carrier via the maleimide group, whereas
  if the enzyme contains a maleimide group, a thiol group is introduced into the carrier such that the enzyme is covalently conjugated to the carrier via the thiol group;

further introducing a maleimide group into at least one amino group remaining in the above complex; and covalently conjugating a reduced antibody, or antibody fragment thereto via a thiol group.

* * * * *

UNITED STATES PATENT AND TRADEMARK OFFICE
CERTIFICATE OF CORRECTION

PATENT NO. : 6,252,053 B1
DATED : June 26, 2001
INVENTOR(S) : Hirokazu Ohbayashi et al.

It is certified that error appears in the above-identified patent and that said Letters Patent is hereby corrected as shown below:

<u>Column 8,</u>
Line 54, after "enzyme-polylysine-antibody" insert -- complex, --;
Line 56, after "complex" insert -- , --.

<u>Column 10,</u>
Line 9, change "it" to -- if --.

Signed and Sealed this

Twenty-first Day of May, 2002

Attest:

Attesting Officer

JAMES E. ROGAN
*Director of the United States Patent and Trademark Office*